(12) United States Patent
Nguyen

(10) Patent No.: US 10,849,634 B2
(45) Date of Patent: Dec. 1, 2020

(54) COUPLING PORTION FOR ROTARY SURGICAL CUTTING SYSTEMS

(71) Applicant: Medtronic Xomed, Inc., Jacksonville, FL (US)

(72) Inventor: Thoai Nguyen, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 40 days.

(21) Appl. No.: 16/013,253

(22) Filed: Jun. 20, 2018

(65) Prior Publication Data

US 2019/0388115 A1 Dec. 26, 2019

(51) Int. Cl.
*A61B 17/16* (2006.01)

(52) U.S. Cl.
CPC ........ *A61B 17/1622* (2013.01); *A61B 17/162* (2013.01); *A61B 17/1617* (2013.01); *A61B 17/1624* (2013.01); *A61B 17/1628* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1631; A61B 17/1633; A61B 17/1655; A61B 17/1657
See application file for complete search history.

(56) References Cited

U.S. PATENT DOCUMENTS

| | | | |
|---|---|---|---|
| 233,709 A * | 10/1880 | Starr | A61C 1/141 433/128 |
| 288,676 A | 11/1883 | Stearns | |
| 1,043,098 A | 11/1912 | Gross | |
| 1,053,709 A | 2/1913 | Collins | |
| 1,112,349 A | 9/1914 | Barnes | |
| 1,209,362 A | 12/1916 | Turner | |
| 1,539,439 A | 5/1925 | Smith | |
| 1,862,337 A | 6/1932 | Emrick | |
| 2,477,058 A | 7/1949 | Harborne et al. | |
| 2,512,033 A | 6/1950 | Metz | |
| 2,522,388 A | 9/1950 | Madsen | |

(Continued)

FOREIGN PATENT DOCUMENTS

| | | |
|---|---|---|
| CH | 686113 | 1/1996 |
| DE | 8815261.8 | 3/1989 |

(Continued)

OTHER PUBLICATIONS

International Search Report and Written Opinion for International Application No. PCT/US2016/018686 dated Jul. 22, 2016 (17 pages).

(Continued)

*Primary Examiner* — Eric S Gibson
(74) *Attorney, Agent, or Firm* — Dicke, Billig & Czaja, PLLC

(57) ABSTRACT

Aspects of the disclosure relate to surgical cutting systems having a surgical tool and a powered hand piece. The surgical tool can include a cutting tool having a coupling portion for selective connection to a drive pin of the hand piece. The coupling portion defines a tang that is configured to promote self-alignment of the cutting tool and the drive pin during connection of the cutting tool and the hand piece, thus promoting ease of use.

20 Claims, 11 Drawing Sheets

(56) References Cited

U.S. PATENT DOCUMENTS

| | | | |
|---|---|---|---|
| 2,596,594 A | 5/1952 | Petre | |
| 2,682,184 A | 6/1954 | Szarkowski | |
| 2,726,872 A | 12/1955 | Onsrud | |
| 2,766,791 A | 10/1956 | Givens | |
| 2,773,693 A | 12/1956 | Chittenden | |
| 3,043,634 A | 7/1962 | Coley | |
| 3,136,347 A | 6/1964 | Linguist | |
| 3,589,826 A | 6/1971 | Fenn | |
| 3,637,225 A | 1/1972 | Schmuck | |
| 3,835,858 A * | 9/1974 | Hagen | A61B 17/1633 606/180 |
| 3,943,986 A * | 3/1976 | Lejdegard | B25B 23/0035 81/438 |
| 4,035,100 A | 7/1977 | Kruger et al. | |
| 4,047,722 A | 9/1977 | Nielsen et al. | |
| 4,078,593 A | 3/1978 | Benitz | |
| 4,107,949 A | 8/1978 | Wanner et al. | |
| 4,123,074 A | 10/1978 | Wanner | |
| 4,146,240 A | 3/1979 | Nielsen | |
| 4,185,383 A | 1/1980 | Heimke et al. | |
| 4,378,053 A | 3/1983 | Simpson | |
| 4,502,734 A | 3/1985 | Allen | |
| 4,512,692 A | 4/1985 | Nielsen et al. | |
| 4,565,472 A | 1/1986 | Brennsteiner et al. | |
| 4,594,036 A | 6/1986 | Hogenhout | |
| 4,655,651 A | 4/1987 | Hunger et al. | |
| 4,823,468 A | 4/1989 | Kollegger | |
| 4,830,000 A | 5/1989 | Shutt | |
| 4,917,274 A | 4/1990 | Asa et al. | |
| 5,009,440 A | 4/1991 | Manschitz | |
| 5,116,353 A | 5/1992 | Green | |
| 5,203,654 A | 4/1993 | Henderson | |
| 5,256,147 A | 10/1993 | Vidal et al. | |
| 5,263,786 A | 11/1993 | Kageyama | |
| 5,286,145 A | 2/1994 | Kleine | |
| 5,352,234 A | 10/1994 | Scott | |
| 5,382,249 A | 1/1995 | Fletcher | |
| 5,421,682 A | 6/1995 | Obermeier et al. | |
| 5,439,005 A | 8/1995 | Vaughn | |
| 5,466,101 A * | 11/1995 | Meyen | B25D 17/088 279/19.4 |
| 5,487,626 A | 1/1996 | Von Holst et al. | |
| 5,499,985 A | 3/1996 | Hein et al. | |
| 5,505,737 A | 4/1996 | Gosselin et al. | |
| 5,549,634 A | 8/1996 | Scott et al. | |
| 5,569,256 A | 10/1996 | Vaughn et al. | |
| D377,982 S | 2/1997 | Walen | |
| 5,601,560 A * | 2/1997 | Del Rio | A61B 17/162 408/231 |
| 5,634,933 A * | 6/1997 | McCombs | A61B 17/162 408/226 |
| 5,697,158 A | 12/1997 | Klinzing et al. | |
| 5,720,749 A | 2/1998 | Rupp | |
| 5,735,535 A | 4/1998 | McCombs et al. | |
| 5,741,263 A * | 4/1998 | Umber | A61B 17/162 279/75 |
| 5,782,836 A | 7/1998 | Umber et al. | |
| 5,807,040 A | 9/1998 | Bongers-Ambrosius et al. | |
| 5,810,802 A | 9/1998 | Panescu et al. | |
| 5,833,704 A | 11/1998 | McCombs et al. | |
| 5,888,200 A * | 3/1999 | Walen | A61B 17/1622 606/167 |
| 5,893,851 A | 4/1999 | Umber et al. | |
| 5,928,241 A * | 7/1999 | Menut | A61B 17/162 279/143 |
| 5,941,891 A * | 8/1999 | Walen | A61B 17/1622 606/167 |
| 5,989,257 A | 11/1999 | Tidwell et al. | |
| 6,000,940 A | 12/1999 | Buss et al. | |
| 6,007,541 A | 12/1999 | Scott | |
| 6,033,408 A * | 3/2000 | Gage | A61B 17/162 173/218 |
| 6,062,575 A | 5/2000 | Mickel et al. | |
| 6,209,886 B1 | 4/2001 | Estes et al. | |
| 6,261,035 B1 | 7/2001 | Moores et al. | |
| 6,267,763 B1 | 7/2001 | Castro | |
| RE37,358 E * | 9/2001 | Del Rio | A61B 17/162 408/231 |
| 6,290,525 B1 | 9/2001 | Jacobi | |
| 6,409,221 B1 | 6/2002 | Robinson et al. | |
| 6,447,484 B1 | 9/2002 | Briscoe et al. | |
| 6,607,533 B2 | 8/2003 | Del Rio et al. | |
| 6,612,588 B2 | 9/2003 | Ostermeier et al. | |
| 6,688,610 B2 | 2/2004 | Huggins et al. | |
| 6,723,101 B2 | 4/2004 | Fletcher et al. | |
| 6,733,218 B2 | 5/2004 | Del Rio et al. | |
| D492,412 S | 6/2004 | Desoutter et al. | |
| 6,746,153 B2 | 6/2004 | Del Rio et al. | |
| 6,780,189 B2 | 8/2004 | Tidwell et al. | |
| 6,811,190 B1 | 11/2004 | Ray et al. | |
| 6,976,815 B2 | 12/2005 | Berglow et al. | |
| 7,001,391 B2 * | 2/2006 | Estes | A61B 17/162 606/167 |
| 7,011,661 B2 * | 3/2006 | Riedel | A61B 17/162 606/170 |
| 7,066,940 B2 * | 6/2006 | Riedel | A61B 17/162 606/167 |
| D536,791 S | 2/2007 | Eskridge et al. | |
| 7,261,169 B2 | 8/2007 | Kleine et al. | |
| 7,374,375 B2 | 5/2008 | Kleine et al. | |
| 7,429,154 B2 | 9/2008 | Kleine et al. | |
| 7,465,309 B2 | 12/2008 | Walen | |
| 7,488,327 B2 | 2/2009 | Rathbun et al. | |
| 7,497,860 B2 | 3/2009 | Carusillo et al. | |
| 7,549,992 B2 | 6/2009 | Shores et al. | |
| 7,559,927 B2 * | 7/2009 | Shores | A61B 17/162 606/79 |
| D609,810 S | 2/2010 | Cote et al. | |
| 7,669,308 B2 | 3/2010 | Oshnock et al. | |
| 7,691,106 B2 | 4/2010 | Schenberger et al. | |
| 7,722,054 B2 | 5/2010 | Young | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| 7,766,585 B2 * | 8/2010 | Vasudeva | B23B 31/005 279/22 |
| D631,962 S | 2/2011 | Dorman | |
| D636,082 S | 4/2011 | Cote | |
| 7,922,720 B2 | 4/2011 | May et al. | |
| D641,468 S | 7/2011 | Ruiz, Sr. et al. | |
| 8,043,292 B2 | 10/2011 | Carusillo | |
| D648,021 S | 11/2011 | Dorman | |
| D666,294 S | 8/2012 | Miles et al. | |
| 8,361,068 B2 | 1/2013 | McClurken | |
| 8,419,760 B2 | 4/2013 | Wiebe, III | |
| 8,518,065 B2 | 8/2013 | Shores et al. | |
| D692,134 S | 10/2013 | Lee-Sepsick | |
| 8,597,316 B2 | 12/2013 | McCombs | |
| 8,702,710 B2 | 4/2014 | Carusillo | |
| 8,801,713 B2 * | 8/2014 | del Rio | A61B 17/1615 606/80 |
| 8,893,820 B2 | 11/2014 | Barhitte et al. | |
| D728,098 S | 4/2015 | Schad et al. | |
| D728,099 S | 4/2015 | Schad et al. | |
| D744,650 S | 12/2015 | Catron et al. | |
| D746,457 S | 12/2015 | Swick et al. | |
| D747,477 S | 1/2016 | Freigang et al. | |
| D753,826 S | 4/2016 | Eggeling et al. | |
| 9,333,561 B2 | 5/2016 | Nakai et al. | |
| 10,080,579 B2 * | 9/2018 | Cihak | B23B 31/005 |
| 10,314,610 B2 * | 6/2019 | Dexter | A61B 17/3205 |
| 10,588,640 B2 * | 3/2020 | Steinhauser | A61B 17/162 |
| 2002/0105149 A1 | 8/2002 | Karst | |
| 2002/0151902 A1 | 10/2002 | Riedel et al. | |
| 2002/0171208 A1 | 11/2002 | Lechot et al. | |
| 2003/0060841 A1 * | 3/2003 | Del Rio | A61B 17/162 606/167 |
| 2003/0097133 A1 | 5/2003 | Green et al. | |
| 2003/0130663 A1 * | 7/2003 | Walen | A61B 17/1615 606/80 |

(56) References Cited

U.S. PATENT DOCUMENTS

| | | | |
|---|---|---|---|
| 2003/0140743 A1* | 7/2003 | Ofentavsek | B25B 15/02 |
| | | | 81/436 |
| 2003/0163134 A1 | 8/2003 | Riedel et al. | |
| 2003/0229351 A1* | 12/2003 | Tidwell | A61B 17/162 |
| | | | 606/80 |
| 2005/0027282 A1 | 2/2005 | Schweikert et al. | |
| 2005/0072007 A1 | 4/2005 | Proulx | |
| 2005/0232715 A1* | 10/2005 | Baumann | B25D 17/088 |
| | | | 408/226 |
| 2006/0053974 A1* | 3/2006 | Blust | A61B 17/162 |
| | | | 81/3.07 |
| 2007/0172321 A1 | 7/2007 | Nagai | |
| 2007/0282329 A1 | 12/2007 | Kawano | |
| 2008/0033280 A1 | 2/2008 | Lubock et al. | |
| 2009/0024129 A1 | 1/2009 | Gordon et al. | |
| 2009/0312779 A1 | 12/2009 | Boykin et al. | |
| 2010/0063524 A1* | 3/2010 | McCombs | A61B 17/162 |
| | | | 606/167 |
| 2010/0076477 A1* | 3/2010 | Jezierski | A61B 17/1631 |
| | | | 606/180 |
| 2011/0022069 A1 | 1/2011 | Mitusina | |
| 2011/0190803 A1 | 8/2011 | To et al. | |
| 2011/0218562 A1 | 9/2011 | Viola et al. | |
| 2011/0238070 A1 | 9/2011 | Santangelo et al. | |
| 2011/0270293 A1* | 11/2011 | Malla | A61B 17/32002 |
| | | | 606/170 |
| 2011/0270294 A1 | 11/2011 | Rubin | |
| 2012/0070220 A1 | 3/2012 | Ruiz, Sr. et al. | |
| 2012/0259336 A1* | 10/2012 | del Rio | A61B 17/162 |
| | | | 606/80 |
| 2012/0259337 A1* | 10/2012 | del Rio | A61B 17/1615 |
| | | | 606/80 |
| 2013/0110147 A1 | 5/2013 | Dame | |
| 2013/0116659 A1 | 5/2013 | Porter | |
| 2013/0138096 A1 | 5/2013 | Benn | |
| 2013/0144267 A1 | 6/2013 | Chan et al. | |
| 2013/0296848 A1 | 11/2013 | Allen, IV et al. | |
| 2014/0056656 A1 | 2/2014 | Bae et al. | |
| 2014/0124231 A1 | 5/2014 | Hessenberger et al. | |
| 2014/0163558 A1 | 6/2014 | Cosgrove et al. | |
| 2014/0303624 A1 | 10/2014 | del Rio et al. | |
| 2014/0336654 A1 | 11/2014 | Pilgeram | |
| 2014/0343454 A1 | 11/2014 | Miller et al. | |
| 2014/0350561 A1 | 11/2014 | Dacosta et al. | |
| 2014/0371752 A1 | 12/2014 | Anderson | |
| 2016/0278802 A1* | 9/2016 | Cihak | A61B 17/32002 |
| 2019/0388115 A1* | 12/2019 | Nguyen | A61B 17/162 |

FOREIGN PATENT DOCUMENTS

| | | |
|---|---|---|
| DE | 102012101259 | 8/2013 |
| EP | 0293327 | 11/1988 |
| EP | 0216354 | 7/1991 |
| EP | 1101459 | 2/2006 |
| EP | 1289714 | 8/2008 |
| EP | 1514034 | 10/2011 |
| FR | 1330849 | 6/1963 |
| GB | 2129730 | 5/1984 |
| GB | 2491524 A | 12/2012 |
| JP | 2014-516611 | 7/2014 |
| RU | 2077275 | 4/1997 |
| WO | 9608343 | 3/1996 |
| WO | 2001/66024 | 9/2001 |
| WO | 2001/89769 | 11/2001 |
| WO | 2007002230 A1 | 1/2007 |
| WO | 2009012457 A1 | 1/2009 |
| WO | 2012/138337 | 10/2012 |
| WO | 2014037134 | 3/2014 |
| WO | 2014176060 | 10/2014 |

OTHER PUBLICATIONS

International Search Report and Written Opinion for International Application No. PCT/US2019/031473 dated Aug. 19, 2019 (12 pages).

Product Catalog—vol. 9, Brasseler USA, Case 0:11-cv-01404-MJD-FLN Document 40-3 Filed Nov. 18, 2011—7 pgs.

* cited by examiner

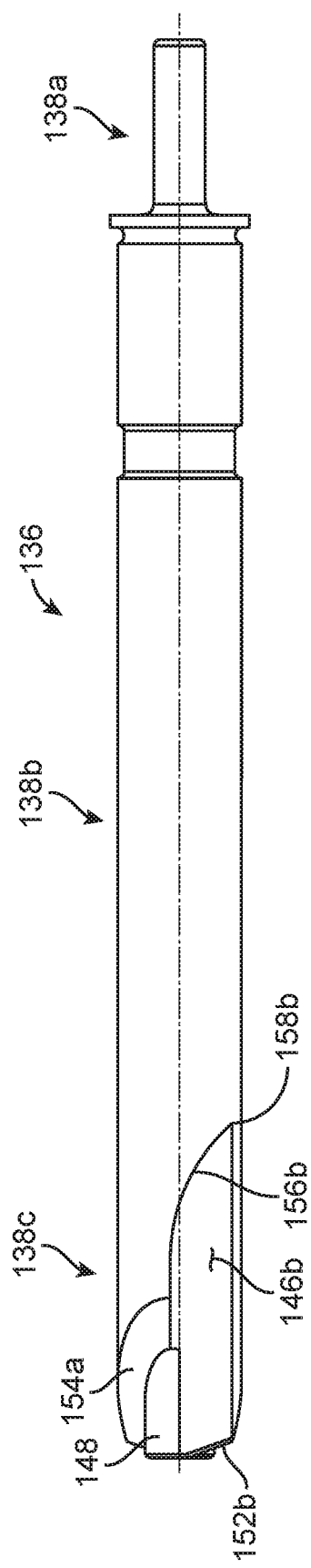
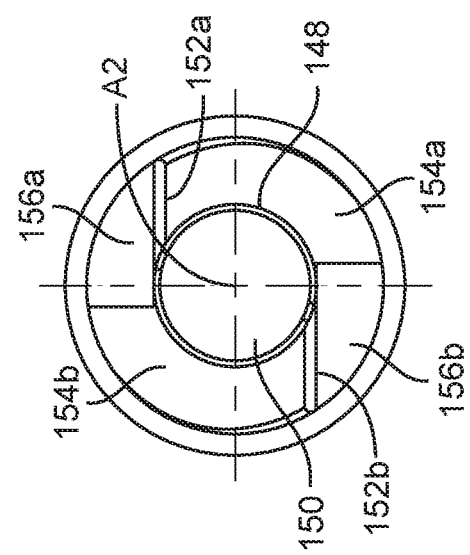
FIG. 3F
FIG. 3G

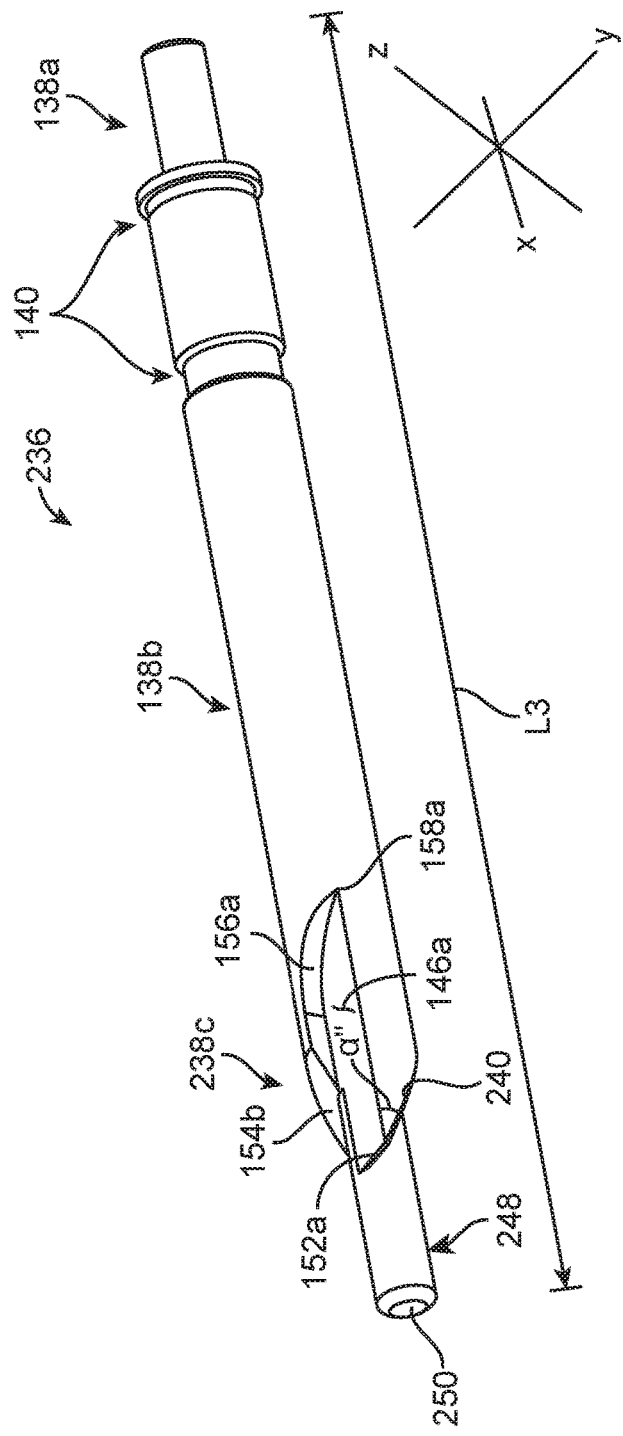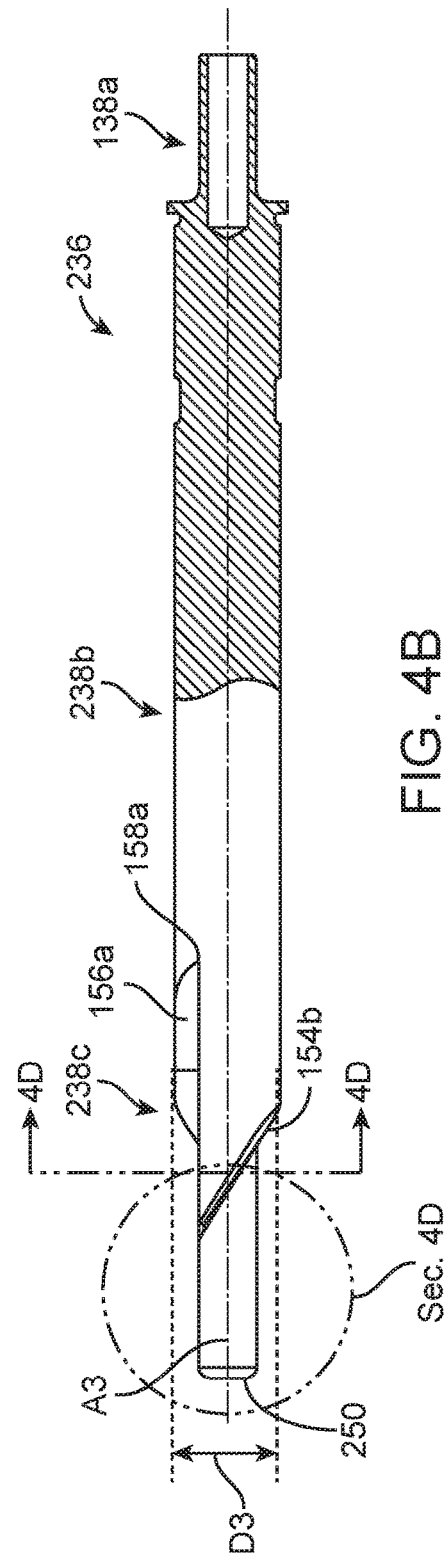
FIG. 4A
FIG. 4B

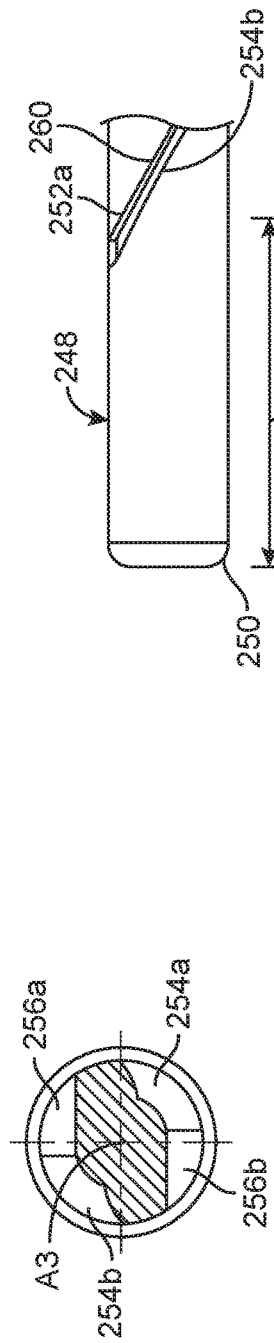
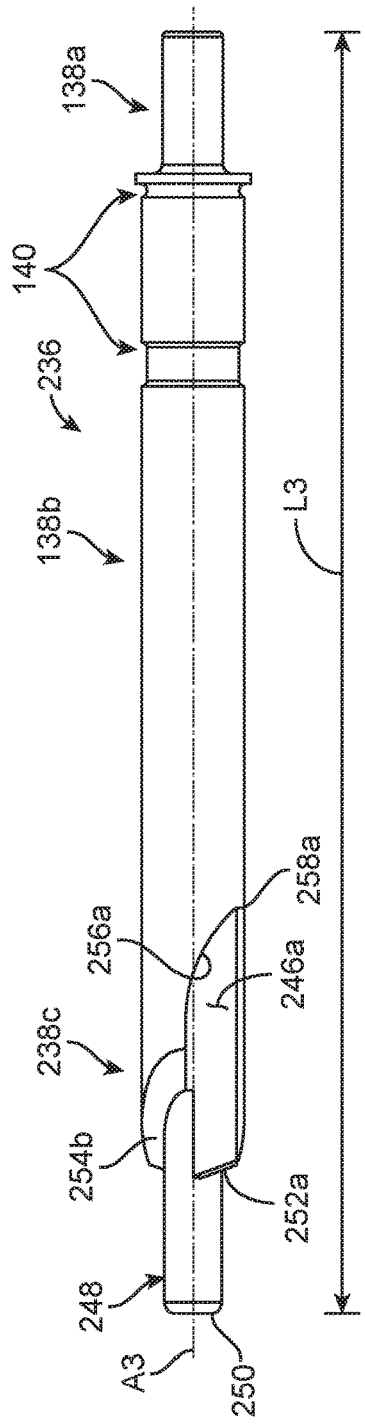
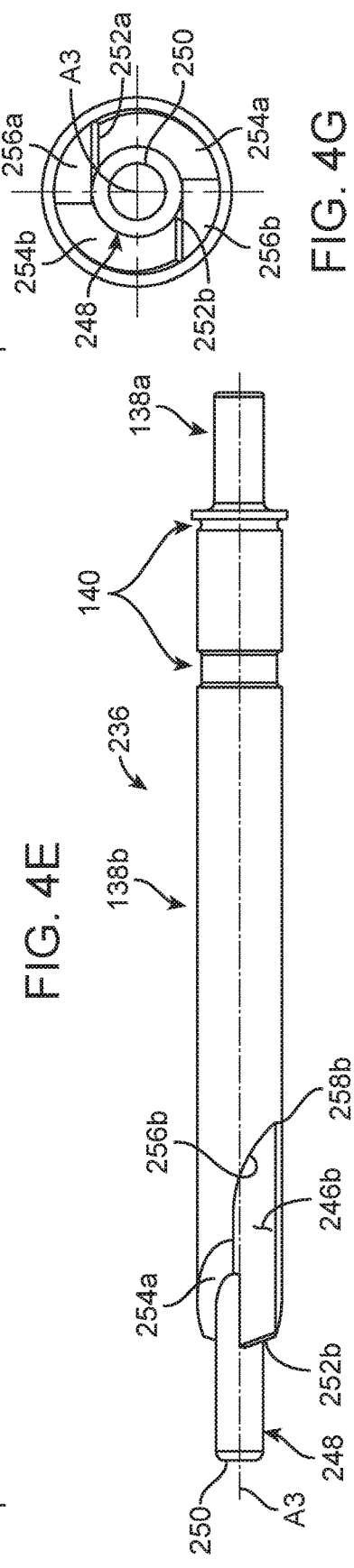

COUPLING PORTION FOR ROTARY
SURGICAL CUTTING SYSTEMS

BACKGROUND

Powered surgical hand pieces are commonly used in many medical specialties to drive surgical tools. For example, powered surgical hand pieces are used to drive surgical drills, blades or other cutting tools in performing various diverse cutting-type functions including drilling, tapping, resection, dissection, debridement, shaving, pulverizing, and shaping of anatomical tissue including bone. The hand pieces are typically configured for selective coupling to, and driving of, a variety of different rotary-type surgical cutting instruments that are each designed to perform a specific procedure. During use, based upon the specific surgical procedure, the surgeon selects the appropriate surgical tool and mounts it to the powered hand piece. The powered hand piece is then operated to move (e.g., rotation, oscillation) the tool in performing the surgical procedure. Additional procedural steps can later be performed by mounting a differently-styled tool to the same powered hand piece.

The improved capabilities of powered surgical hand pieces, as well as the vast number of surgical cutting tools now available, have undoubtedly greatly increased the number of neurological, spine, ENT/head/neck and other procedures that a surgeon can perform utilizing a single surgical system (i.e., a single powered hand piece with multiple surgical cutting tools). Selective driven coupling between the powered hand piece and each tool is typically effectuated within a housing of the hand piece. The housing carries an internal drive chuck or the like configured to receive a shank of the surgical cutting tool in a mating fashion. Thus, the shank of each surgical cutting tool useful with a particular hand piece generally has a common cross-sectional shape, with this shape corresponding to the hand piece drive chuck (e.g., circular, hexagonal). The drive chuck is connected to (or formed as part of) a drive shaft; upon connection of the surgical cutting tool to the drive chuck, powered rotation of the drive shaft rotates the cutting tool.

In current approaches, the cutting tool, including the shank, is generally shaped as an elongated cylinder defining a single central axis about which the tool is rotated during use. The hand piece drive chuck forms a corresponding, generally cylindrical-shaped passage for receiving the shank, effectuating a coupled connection and subsequent driven interface at point contacts created solely about the single central axis. The shank (or other regions of the cutting tool) may include recesses, grooves, or other features deviating from a truly cylindrical shape for purposes of effectuating an axial and/or rotational lock relative to the drive chuck. In some instances, alignment of the shank and drive chuck can be problematic, leading to user frustration.

The present disclosure addresses problems and limitations associated with the related art.

SUMMARY

Aspects of the disclosure relate to a surgical cutting tool that includes a body and a cutting head. The body maintains a coupling portion, which can selectively connect the surgical cutting tool to a powered hand piece to form a surgical cutting system. A tang of the coupling portion is configured such that upon insertion of the tang into a drive pin of the hand piece, the tang promotes self-alignment of the coupling portion with the drive pin.

In one illustrative embodiment, the coupling portion includes a tang and a distal portion interconnected by an intermediate stem portion. The intermediate stem portion defines a central axis. The tang includes an extension portion coaxially aligned with the central axis and a first interface surface defining a first plane that is parallel with the central axis. The first interface surface terminates at a first end surface oriented perpendicular to the first plane. The tang further includes a first ramp portion extending distally from the first end surface adjacent the extension portion at a first angle of about 5 to about 85 degrees with respect to the first interface surface. A second interface surface is further provided defining a second plane that is parallel with the central axis. The second interface surface terminates at a second end surface oriented perpendicular to the second plane. The tang further includes a second ramp portion extending distally from the second end surface adjacent the extension portion at a second angle of about 5 to about 85 degrees.

A surgical cutting system for use in the dissection of bone, biomaterials, and/or other tissue is provided in yet another illustrative embodiment. The surgical cutting system includes a hand piece including a drive pin, a cutting tool including a cutting head and a coupling portion coupled to the cutting head such that rotation of the coupling portion correspondingly rotates the cutting head. The coupling portion can releasably connect the cutting tool to the hand piece. The coupling portion includes a tang and a distal portion interconnected by an intermediate stem portion; wherein the intermediate stem portion defines a central axis. The tang includes an extension portion coaxially aligned with the central axis and a first interface surface defining a first plane that is parallel with the central axis. The first interface surface terminates at a first end surface oriented perpendicular to the first plane and the tang further includes a first ramp portion extending distally from the first end surface adjacent the extension portion at a first angle of about 5 to about 85 degrees with respect to the first interface surface. The tang also includes a second interface surface defining a second plane that is that is parallel with the central axis; the second interface surface terminating at a second end surface oriented perpendicular to the second plane. The tang includes a second ramp portion extending distally from the second end surface adjacent the extension portion at a second angle of about 5 to about 85 degrees.

BRIEF DESCRIPTION OF THE DRAWINGS

FIG. 3F is a bottom view of the coupling portion of FIGS. 3A-3B and 3E.

FIG. 3G is an end view of the coupling portion of FIG. 3A.

FIG. 4A is an isometric view of an alternate coupling portion.

FIG. 4B is a first side view of the coupling portion of FIG. 4A shown in partial cross-section.

FIG. 4C is a cross-sectional view of the coupling portion of FIG. 4B as viewed from line 4C-4C.

FIG. 4D is an enlarged view of Sec. 4D of FIG. 4B.

FIG. 4E is a top view of the coupling portion of FIGS. 4A-4B.

FIG. 4F is a bottom view of the coupling portion of FIGS. 4A-4B and 4E.

FIG. 4G is an end view of the coupling portion of FIG. 4A.

DETAILED DESCRIPTION

As used throughout this disclosure, the term "edge" is in reference to an outside limit of an object, area or surface. Unless otherwise specifically noted, the term "edge" is not limited to a uniform, linear or straight line, and is inclusive of irregular, curved or complex shapes.

As used throughout this disclosure, the term "surface" or "wall" is in reference to an outer part or extent of a body, having a continuous set of points that has length and breadth, but no thickness. Unless otherwise specifically noted, the term "surface" or "wall" are not limited to a uniform, flat or planar face (as defined by within 5% of a flat or planar surface, and is inclusive of irregular, curved or complex shapes.

Figure 1:
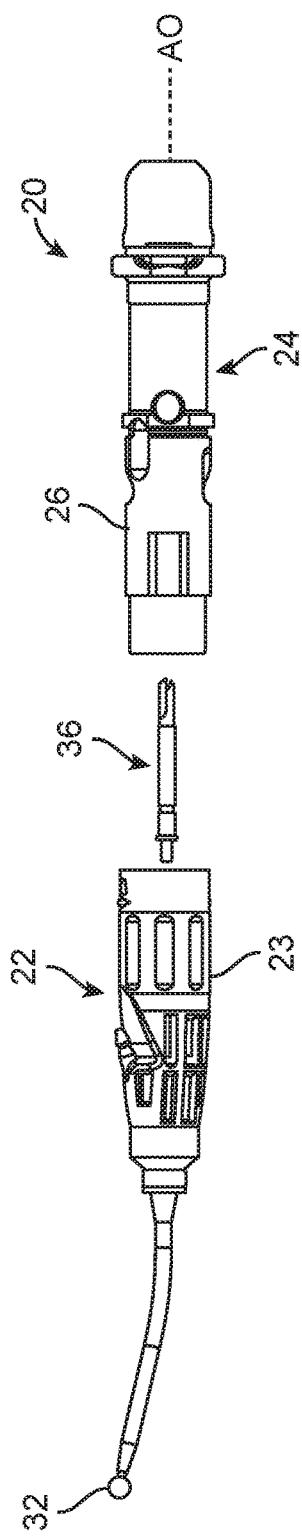
FIG. 1 is a partially-exploded perspective view of a surgical cutting system including a surgical cutting tool having a coupling portion that interconnects the surgical cutting tool to a hand piece.
Figure 2A:
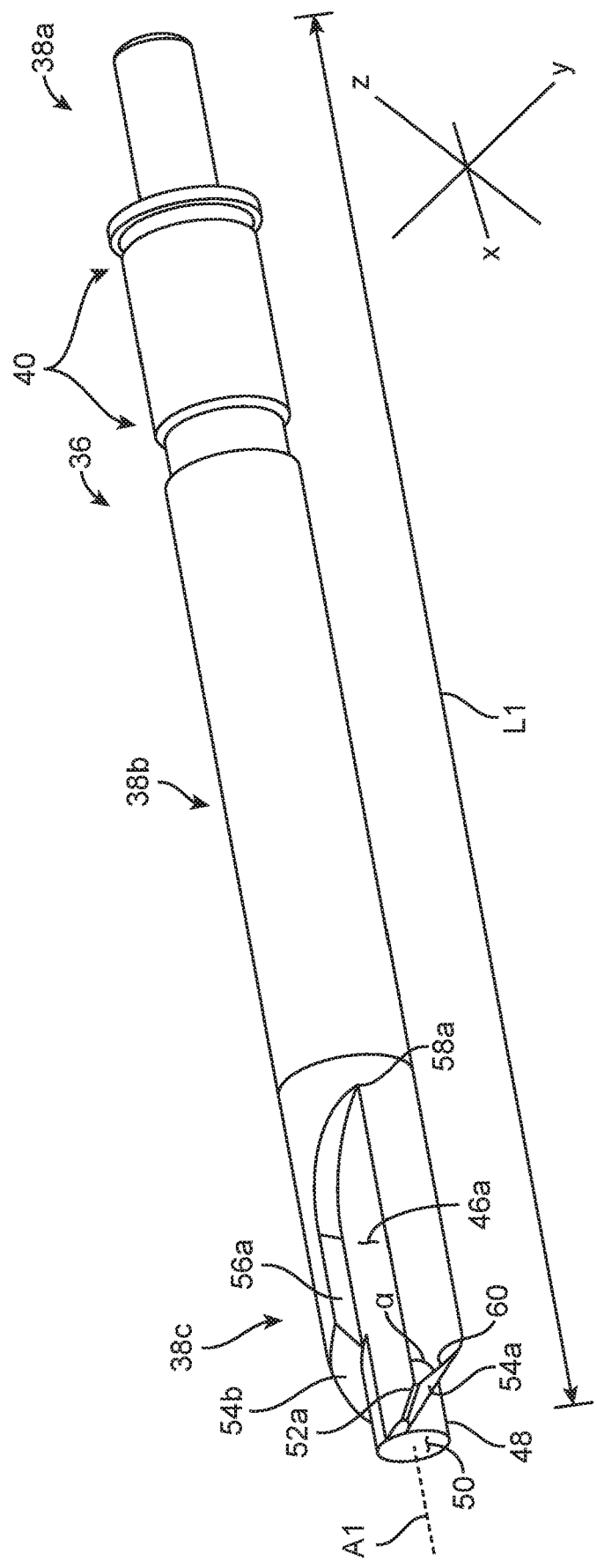
FIG. 2A is an isometric view of the coupling portion of FIG. 1.
Figure 2B:
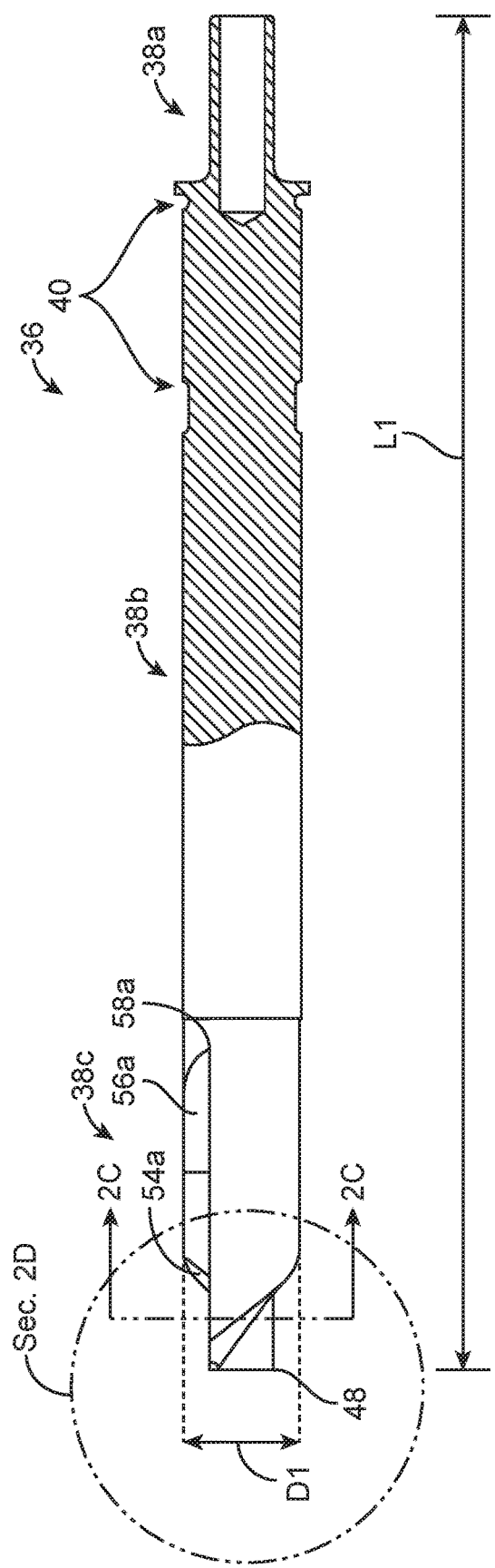
FIG. 2B is a first side view of the coupling portion of FIG. 2A shown in partial cross-section.
Figure 2D:
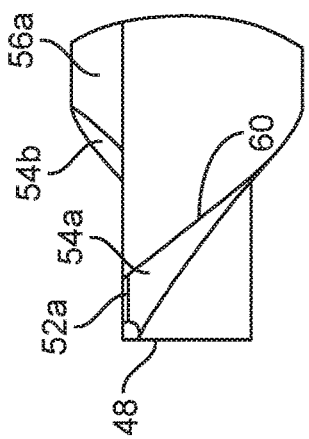
FIG. 2D is an enlarged view of Sec. 2D of FIG. 2B.
Figure 2C:
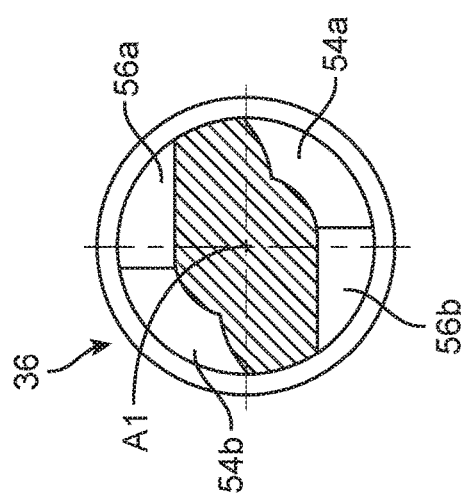
FIG. 2C is a cross-sectional view of the coupling portion of FIG. 2B as viewed from line 2C-2C.
Figure 2E:
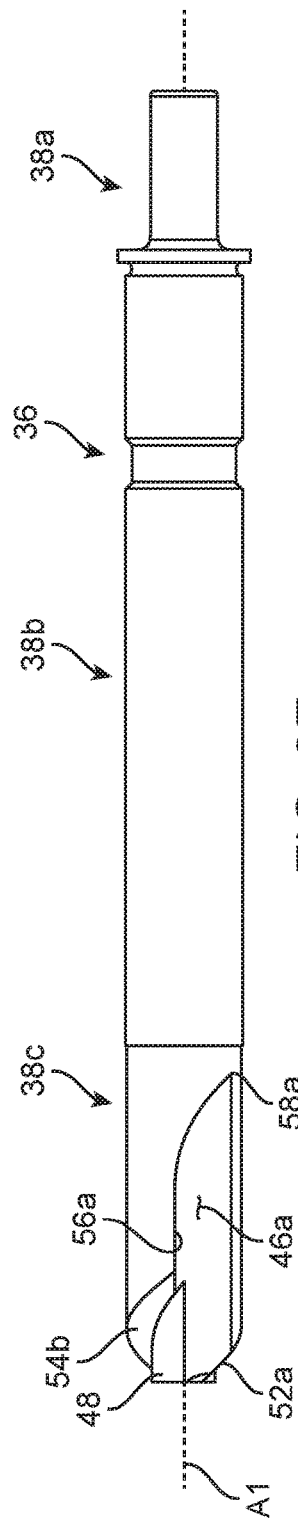
FIG. 2E is a top view of the coupling portion of FIGS. 2A-2B.
Figure 2F:
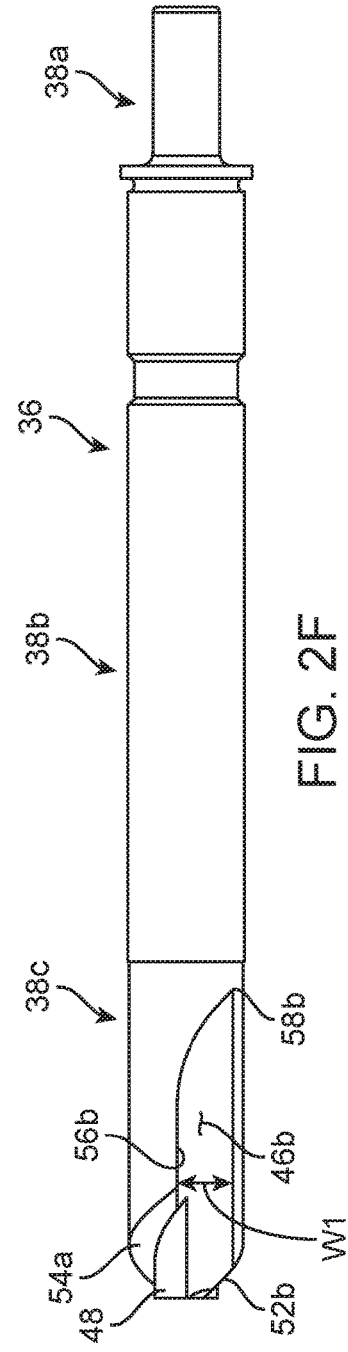
FIG. 2F is a bottom view of the coupling portion of FIGS. 2A-2B and 2E.
Figure 2G:
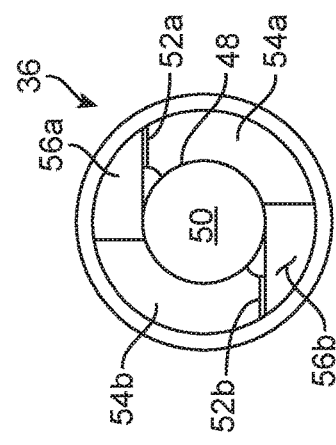
FIG. 2G is an end view of the coupling portion of FIG. 2A.
Figure 3A:
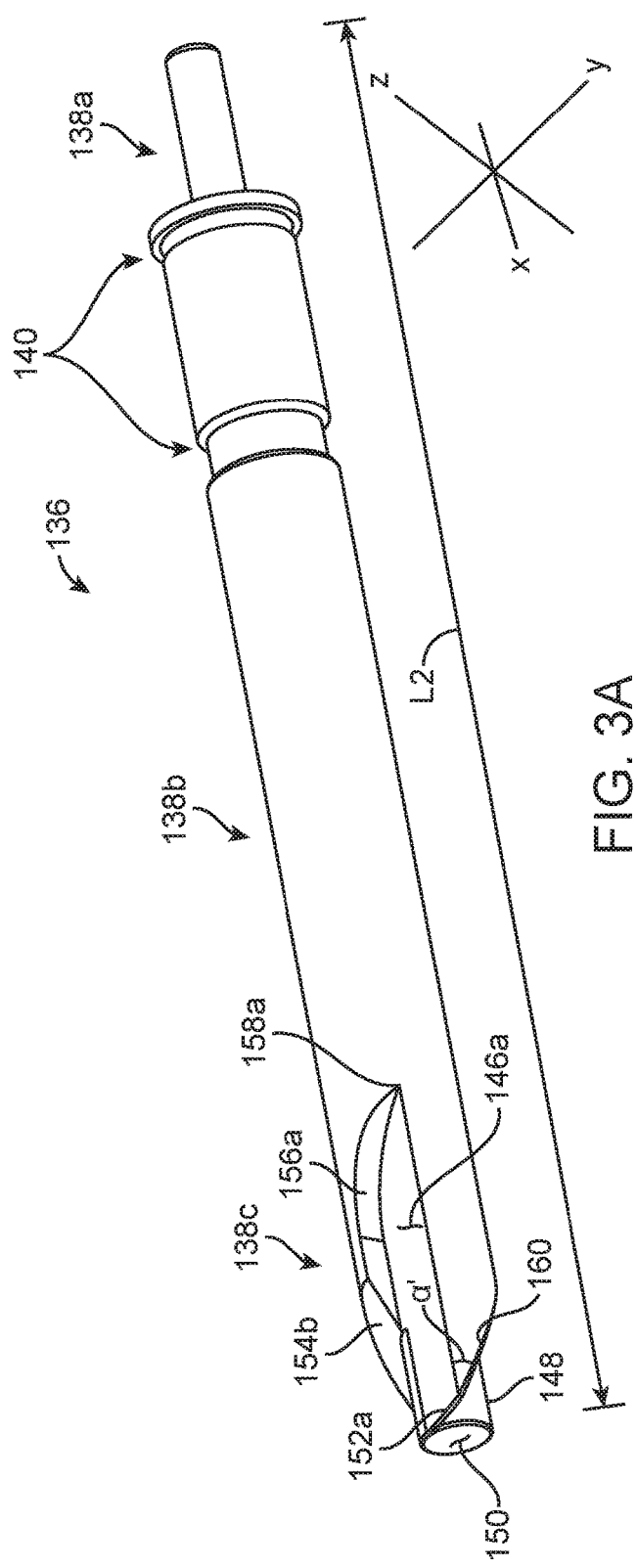
FIG. 3A is an isometric view of an alternate coupling portion.
Figure 3B:
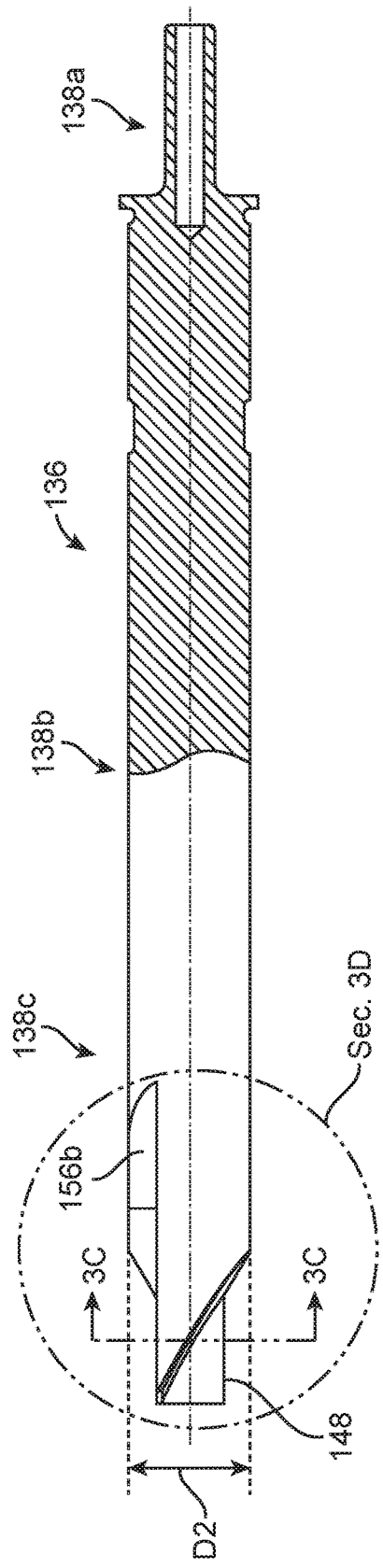
FIG. 3B is a first side view of the coupling portion of FIG. 3A shown in partial cross-section.
Figure 3C:
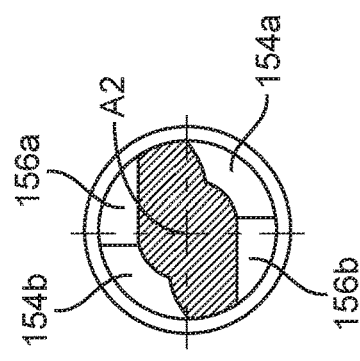
FIG. 3C is a cross-sectional view of the coupling portion of FIG. 3B as viewed from line 3C-3C.
Figure 3D:
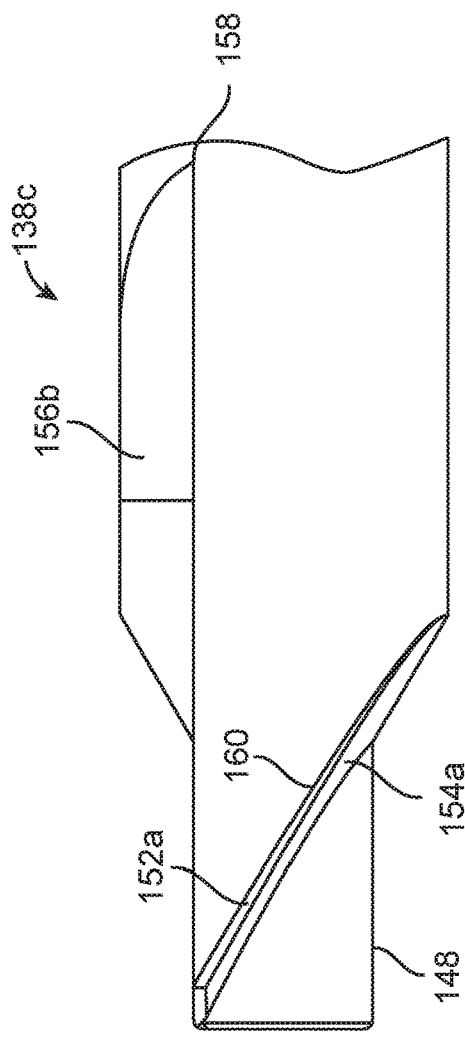
FIG. 3D is an enlarged view of Sec. 3D of FIG. 3B.
Figure 3E:
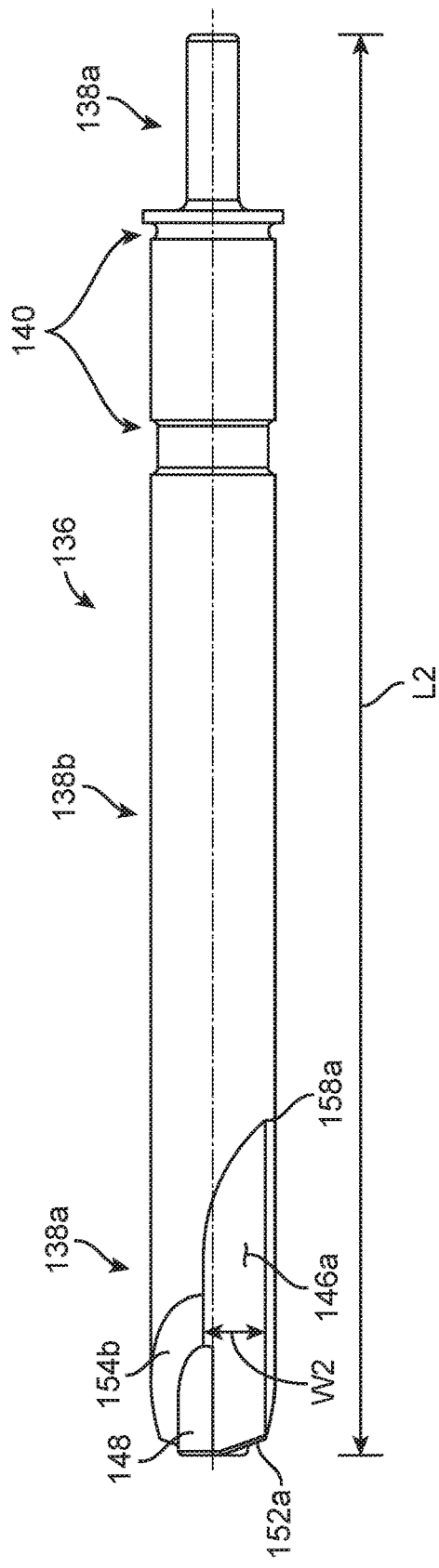
FIG. 3E is a top view of the side of the coupling portion of FIGS. 3A-3B.

One embodiment of a surgical cutting system 20 is shown in FIG. 1, and includes a rotary surgical cutting tool 22 and a powered hand piece 24. Details on the various components are described below. In general terms, the surgical cutting tool 22 is selectively coupled to the hand piece 24 at least in part with a coupling portion 36. Once mounted, the powered hand piece 24 is operated to rotate (e.g., rotate in a single direction or oscillate) the surgical cutting tool 22 in performing a desired surgical procedure. Aspects of the present disclosure are directed toward the coupling between the surgical cutting tool 22 and the powered hand piece 24, and in particular features provided by the coupling portion 36 and the powered hand piece 24 that promote self-alignment of the coupling portion 36 (and thus, the cutting tool 22) when being connected to the hand piece 24.

In some embodiments, the surgical cutting tool 22 includes a body 23 in which an elongated shaft (not visible), which can be connected to the coupling portion 36. The elongated shaft and connecting portion 36 can be formed of a rigid, surgically safe material (e.g., stainless steel). A distal portion of the elongated shaft forms or carries (e.g., has assembled thereto) a cutting head 32. The cutting head 32 can assume a wide variety of forms appropriate for performing a desired rotary surgical cutting procedure (e.g., cutting, debulking, resecting, or removing anatomical tissue including bone). By way of one non-limiting embodiment, the cutting head 32 can be a bur having any shape, size, flute pattern, etc., as desired. While the cutting tool 22 is illustrated as being non-linear or having one bend or curve, in other embodiments the elongated shaft can be linear or define a plurality of bends or curves. The cutting tool 22 can otherwise be of a type known in the art (e.g., model number SP12BA30 available from by Medtronic, Inc. of Minneapolis, Minn.).

Generally, the powered hand piece 24 includes one or more features (e.g., drive pin 70 discussed in greater detail below with respect to FIGS. 6A-7) configured to interface with the surgical cutting tool 22 in selectively receiving/loading the surgical cutting tool 22 and for rotatably driving a loaded surgical cutting tool 22. In this regard, the powered hand piece 24 can employ various drive assemblies or motors (e.g., pneumatically powered or driven, electrically powered or driven, etc.) as known in the art for effectuating driven rotation at desired speeds, and generally includes a housing assembly 26 maintaining a drive shaft (not shown) that mechanically couples or links a motor (not shown) to the drive pin 70 via a coupling assembly. The drive pin 70, in turn, is configured to receive the corresponding surgical cutting tool 22 (e.g., surgical cutting tool 22 via coupling portion 36). The hand piece 24 can otherwise be of a type known in the art (e.g., model number SP12BA30 available from by Medtronic, Inc. of Minneapolis, Minn.).

One embodiment of the coupling portion 36 is shown in greater detail in FIGS. 2A-2G. The coupling portion 36 includes or defines a distal portion or region 38a, an intermediate stem portion or region 38b, and a proximal tang 38c. As a point of reference, the elongated shape of the stem portion 38b serves to generate a longitudinal or length direction "L1", based upon which other geometry features can be identified. For ease of understanding, x, y, and z conventions (FIG. 2A) are provided with the views; the x direction or axis corresponds with the longitudinal or length direction L1. The stem portion 38b can be cylindrical (e.g., an elongated right cylinder), cylindrical-like, or have any other constant shape along at least a majority of a length of the intermediate stem portion 38b in a form that otherwise generates a central axis A1.

A shape of the intermediate stem region 38b can be viewed as defining a maximum outer dimension (e.g., diameter) D1 (FIG. 2B) in a plane perpendicular to the central axis A1 and length direction L1. The central axis A1 can intersect a center point of the maximum outer dimension D1. While the shape of the stem portion 38b is reflected as being generally cylindrical, the intermediate stem portion 38b can have other cross-sectional shapes that establish the maximum outer dimension D1 and that that may not be truly cylindrical in nature. In some embodiments, surface features 40 (distal grooves or engagement features, generally referenced) can optionally be incorporated into the stem portion 38b such that the stem portion 38b need not necessarily have a constant or uniform shape; however, a cross-sectional shape of the intermediate stem portion 38b along at least a majority of the longitudinal length L1 generates the central axis A1.

Figure 5A:
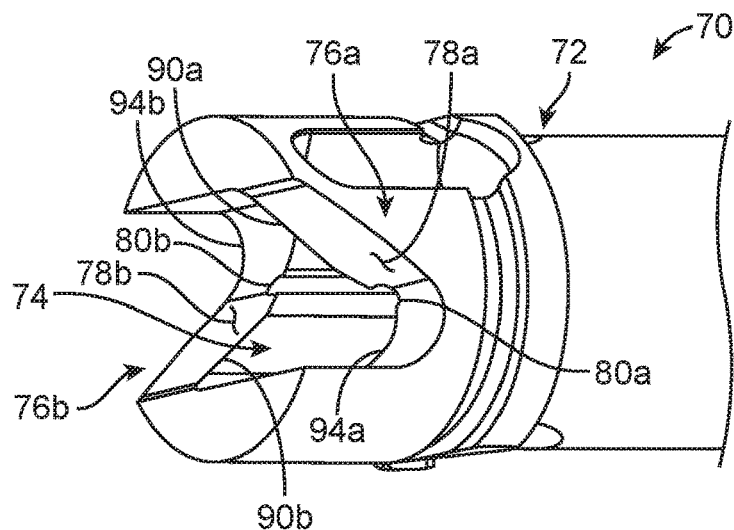
FIG. 5A is a partial, perspective view of a proximal end of a drive pin of a hand piece, for example, the hand piece of FIG. 1.

The tang 38c is configured for establishing a driven interface with the hand piece 24 and, in particular, the drive pin 70, which is best shown in FIGS. 6A-6D and discussed in further detail below. In general terms, however, the tang 38c serves to transfer torque from the hand piece 24 to the cutting tool 22, in which a drive or input torque provided by drive pin 70 to the coupling portion 36 is transferred to the intermediate stem portion 34, and thus a remainder of the cutting tool 22, as a torque about the central axis A1. To this end, the tang 38c forms or includes first and second interface surfaces 46a, 46b that provide torque transfer by engaging the input torque from the motor of the powered hand piece 24 via the drive pin 70. In particular, the first interface surface 46a and the second interface surface 46b are both configured to engage respective guides 76a, 76b of the drive pin 70 (FIG. 5A).

In this example embodiment, two interface surfaces 46a, 46b are provided, each being approximately 180 degrees from one another and each defining a plane that is parallel with the central axis A1. In some embodiments, the maximum width W1 is not less than 0.25 mm. In one embodiment, each interface surface 46a, 46b has a maximum width W1 in the range of about 0.25 mm to about 2.0 mm. The tang 38c further includes an extension portion 48 that is centrally located with respect to the central axis A1. The extension portion 48 of this particular embodiment is cylindrical in shape and has a blunt (i.e. planar) end surface 50 that is perpendicular to the central axis A1. It is envisioned that the extension portion 48 can extend from end surfaces 52a, 52b at a variety of lengths and that the end surface 50 may take a variety of shapes. It can be seen in FIGS. 2E-2F, that in the present embodiment, the extension portion 48 does not extend past the end surfaces 52a, 52b and, thus, has an extension length of about 0 mm. A few examples of alternate embodiments are presented herein. The end surface 52a extends perpendicular from the first interface surface 46a, which is also perpendicular to the central axis A1. The end surface 52a can have a thickness or width in the range of about 0 mm to about 5 mm. A first ramp 54a extends from the end surface 52a, along the extension portion 48 in a linear fashion at an angle α of about 5 to about 85 degrees with respect to the central axis A. In other words, an outer edge 60 of the first ramp 54a is linear. In some embodiments the angle α is about 30 to about 60 degrees. In one example embodiment, the angle α is approximately 45 degrees. Opposite the first end surface 52a, the ramp 54a terminates abutting an interface wall 56b (FIG. 2E), which is arcuate and extends radially outwardly along a proximal edge of the second interface surface 46b. The first interface surface 46a and the interface wall 56a converge at a convergence point 58a, which is located at the distalmost point of the first interface surface 46a. In one embodiment, a shortest distance between the convergence point 58a and end surface 52a is in the range of about 5 mm to about 7 mm.

Similarly, the second interface surface 46b defines an end surface 52b that is oriented perpendicular to the central axis A1. A second ramp 54b extends from the end surface 52b, along the extension portion 48 in a linear fashion and can be identically configured to first ramp 45a. Opposite the second end surface 52b, the ramp 54b terminates abutting an interface wall 56a (FIG. 2D), which is arcuate and extends radially outwardly along a proximal edge of the first interface surface 46a. The second interface surface 46b and the interface wall 56b converge at a convergence point 58b, which is located at the most distal point of the first interface surface 46b. In one embodiment, a shortest distance between the convergence point 58b and end surface 52b is in the range of about 5 mm to about 7 mm. In view of this description and the drawings, it is to be understood that in one illustrative embodiment, the tang 38c includes first and second sides (FIGS. 2E-2F) 180 degrees from one another that are identically configured mirror images of each other. In other words, interface surfaces 46a, 46b are identical, end surfaces 52a, 52b are identical, ramps 54a, 54b are identical, interface walls 56a, 56b are identical and convergence points 58a, 58b are identical.

Referring now also to FIGS. 3A-3G, which illustrate an alternate coupling portion 136 that can be used as an alternate to coupling portion 36. The coupling portion 136 includes and defines a distal portion or region 138a, an intermediate stem portion or region 138b, and a proximal tang 138c. As a point of reference, the elongated shape of the stem portion 138b serves to generate a longitudinal or length direction "L2", based upon which other geometry features can be identified. For ease of understanding, x, y, and z conventions (FIG. 3A) are provided with the views; the x direction or axis corresponds with the longitudinal or length direction L2. The stem portion 138b can be cylindrical (e.g., an elongated right cylinder), cylindrical-like, or have any other constant shape along at least a majority of a length of the intermediate stem portion 38b in a form that otherwise generates a central axis A2.

A shape of the intermediate stem region 138b can be viewed as defining a maximum outer dimension (e.g., diameter) D2 (FIG. 3B) in a plane perpendicular to the central axis A2 and length direction L2. The central axis A2 can intersect a center point of the maximum outer dimension D2. While the shape of the stem portion 138b is reflected as being generally cylindrical, the intermediate stem portion 138b can have other cross-sectional shapes that establish the maximum outer dimension D2 and that that may not be truly cylindrical in nature. In some embodiments, surface features 140 (distal grooves or engagement features, generally referenced) can optionally be incorporated into the stem portion 138b such that the stem portion 138b need not necessarily have a constant or uniform shape; however, a cross-sectional shape of the intermediate stem portion 138b along at least a majority of the longitudinal length L2 generates the central axis A2.

The tang 38c forms or includes first and second interface surfaces 146a, 146b that provide torque transfer by engaging the input torque from the motor of the powered hand piece 24 via the drive pin 70 as discussed above with respect to coupling portion 36. In particular, the first interface surface 146a and the second interface surface 146b are both configured to engage respective guides 76a, 76b of the drive pin 70 (FIG. 5A).

In this embodiment, two interface surfaces 146a, 146b are provided, each being approximately 180 degrees from one another and each defining a plane that is parallel with the central axis A2. In one embodiment, each interface surface 146a, 146b has a maximum width W2 in the range of about 0.25 mm to about 2 mm. The tang 138c further includes an extension portion 148 that is centrally located with respect to the central axis A2. The extension portion 148 of this particular embodiment is cylindrical in shape and has a blunt (i.e. planar) end surface 150 that is perpendicular to the central axis A2. It is envisioned that the extension portion can extend from end surfaces 152a, 152b at a variety of lengths and that the end surface 150 may take a variety of shapes. It can be seen in FIGS. 3E-3F, that in the present embodiment, the extension portion 148 does not extend past the end surfaces 152a, 152b and, thus, has an extension length of about 0 mm. A few examples of alternate embodiments are disclosed herein. The end surface 152a extends perpendicular from the first interface surface 146a, which is also perpendicular to the central axis A2. A first ramp 154a extends from the end surface 152a, along the extension portion 148 in a helical fashion at an angle α' of about 5 to about 85 degrees with respect to the central axis A2. In other words, an outer edge 160 of the first ramp 54a is helical. In some embodiments the angle α' is about 30 to about 60 degrees and the pitch for the helix sweep ranging between 2.5 mm to 7 mm. Opposite the first end surface 152a, the ramp 154a terminates abutting an arcuate interface wall 156b (FIG. 3E), which is arcuate and extends radially outwardly along a proximal edge of the second interface surface 146b. The first interface surface 146a and the interface wall 156a converge at a convergence point 158a, which is located at the distalmost point of the first interface surface 146a. In one embodiment, a shortest distance between the convergence point 158a and end surface 152a is in the range of about 5 mm to about 7 mm. In one example embodiment, the end surface 152a has a thickness or width in the range of about 0 mm to about 5 mm.

Similarly, the second interface surface 146b defines an end surface 152b that is oriented perpendicular to the central axis A2. A second ramp 154b extends from the end surface 152b, along the extension portion 148 in a helical fashion in a manner identical to that of the first ramp 154a. Opposite the second end surface 152b, the ramp 154b terminates abutting an arcuate interface wall 156a (FIG. 3D), which is arcuate and extends radially outwardly along a proximal edge of the first interface surface 146a. The second interface surface 146b and the interface wall 156b converge at a convergence point 158b, which is located at the most distal point of the first interface surface 146b. In one embodiment, a shortest distance between the convergence point 158b and end surface 152b is in the range of about 5 mm to about 7 mm. In view of this description and the drawings, it is to be understood that in one illustrative embodiment, the tang 138c includes first and second sides (FIGS. 3E-3F) 180 degrees from one another that are identically configured mirror images of each other. In other words, interface surfaces 146a, 146b are identical, end surfaces 152a, 152b are identical, ramps 154a, 154b are identical, interface walls 156a, 156b are identical and convergence points 158a, 158b are identical.

Turning now in addition to FIGS. 4A-4G, which illustrate yet another alternate coupling portion 236 that can be used as an alternate to any of the above-disclosed coupling portions 36, 136. As indicated with like reference numerals, the coupling portion 236 of FIG. 4A-4G is largely identical to that of FIGS. 3A-3G with the exception that a tang 238c of the coupling portion 236 includes an extension member 250 having a length L4 that extends past interface surfaces 146a, 146b. This embodiment can be modified in accordance with all previously disclosed embodiments and is configured and operates identically to that of FIGS. 3A-3G except as expressly stated. For example, each ramp 154a, 154b may extend linearly from one respective end surface 152a, 152b along the extension portion 248, as disclosed above with respect to FIGS. 3A-3G.

As previously indicated, the coupling portions 36, 136, 236 disclosed herein can be used to operatively interconnect a cutting tool (e.g., cutting tool 22) to a hand piece (e.g. hand piece 24). In this way, the hand piece 24 can include a drive pin or drive pin 70 configured to receive and interface with the cutting tool 22 via the coupling portion 36, 136, 236. One example of a drive pin 70 is illustrated in FIGS. 5A-7. During operation of the powered hand piece 24, the drive pin 70 rotates about a rotational axis A0 of the hand piece 24 (FIG. 1). The drive pin 70 can be connected to or integrally formed within a powered hand piece (e.g., hand piece 24 or the like). The drive pin 70, shown in cross section in FIG. 5A, has an elongated, generally cylindrical shape and includes a shaft 72 forming a lumen 74. The drive pin 70 defines first and second guides 76a, 76b. Each guide 76a, 76b is optionally identically configured but oriented approximately 180 degrees from one another. In this way, each guide 76a, 76b includes a guide surface 78a, 78b oriented at an angle with respect to the rotational axis A0 of the drive pin 70. At a proximal end of each guide 76a, 76b is a notch 80a, 80b that extends into an inner edge 82a, 82b of the guide surface 78a, 78b. Each guide surface 78a, 78b corresponds to one respective ramp (e.g. 54a) and interface wall (e.g., 56a) of the tang (e.g., 38c) to direct the tang into operational seated alignment as it is being inserted by a user. As will be discussed in greater detail below, operational seated alignment is when each interface wall (e.g., 56a, 56b) is engaged within a respective notch 80a, 80b and each interface wall abuts one respective guide surface 78a, 78b.

Figure 5B:
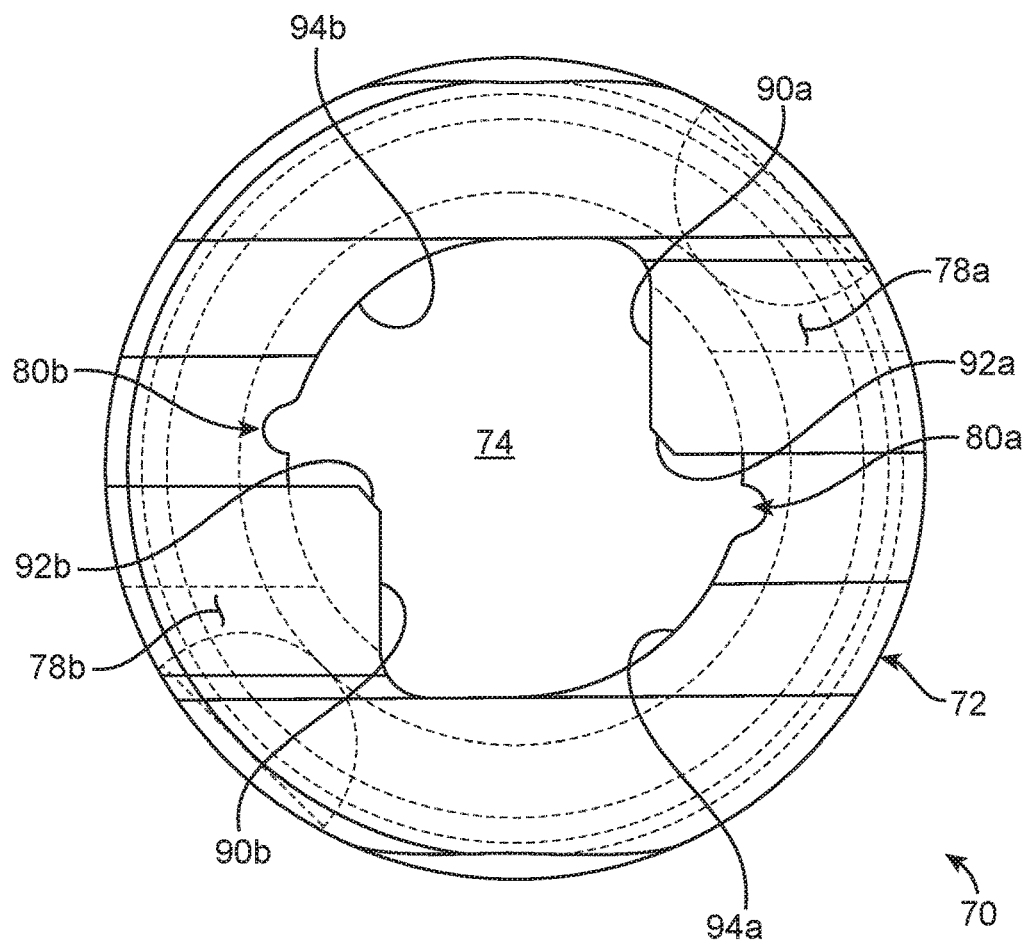
FIG. 5B is an end view of the sectioned drive pin of FIG. 5A.

In one embodiment, the lumen 74 is defined by the combination of a variety of surfaces or edges (e.g., 80a-b, 90a-b, 92a-b, 94a-b) as best seen in FIG. 5B. In one example, the lumen 74 can be described as having two halves, wherein each half includes a drive surface 90a, 90b, protrusion surfaces 92a, 92b, notch 80a, 80b and arcuate inner guide edge 94a, 94b and guide surface 78a, 78b. The drive surfaces 90a 90b are generally parallel to one another and also the protrusion surfaces 92a, 92b are also parallel with respect to each other. Each guide surface 78a, 78b projects within the lumen 74.

Figure 6A:
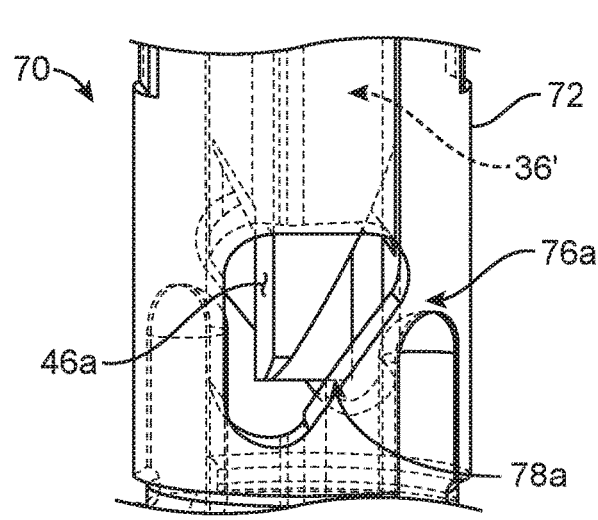
FIGS. 6A-6D illustrate a coupling portion being inserted into the drive pin of FIGS. 5A-5B and how the coupling portion self-aligns to engage the drive pin.
Figure 6B:
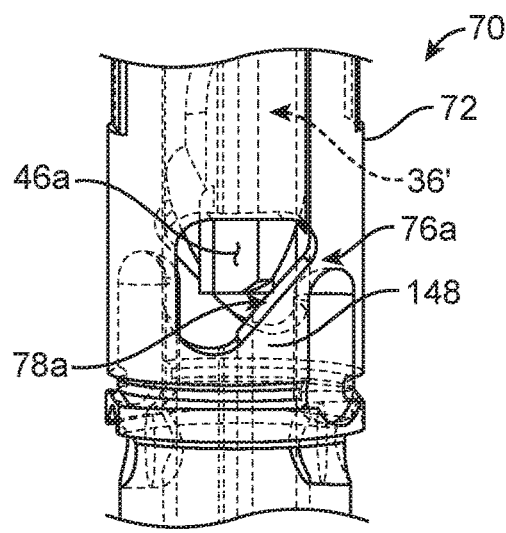
Figure 6C:
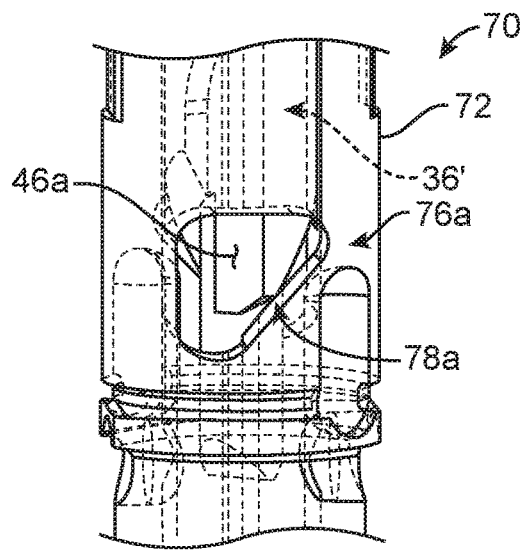
Figure 6D:
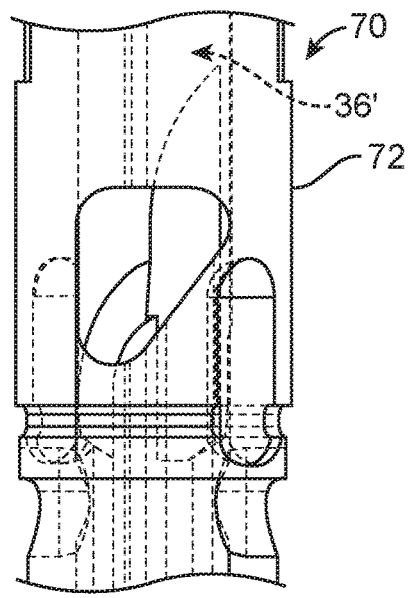
Figure 7:
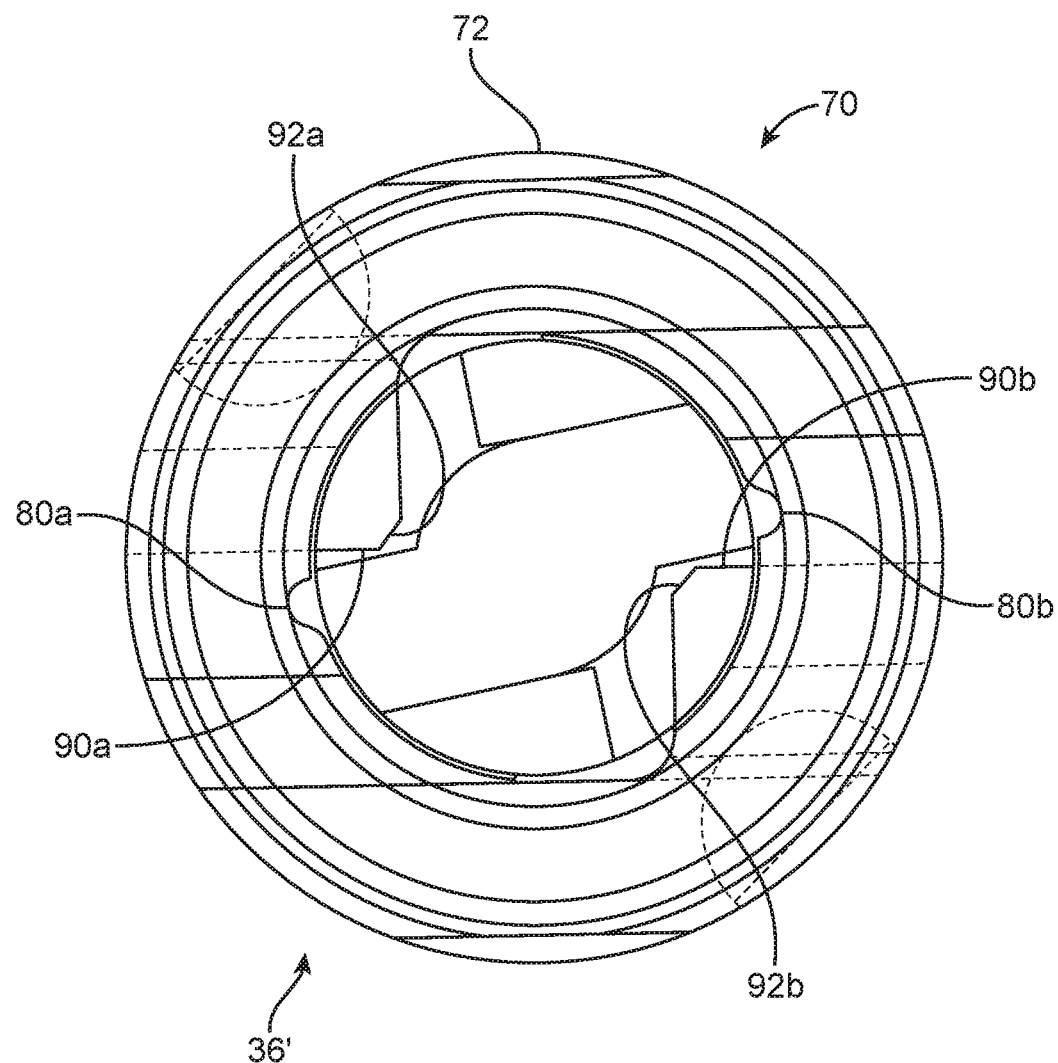
FIG. 7 is an end view of the coupling portion of FIGS. 6A-6D almost, but not engaged with the drive pin of FIGS. 5A-5B.

Referring now also to FIGS. 6A-7, which illustrate stages of engagement of a coupling portion 36' with the drive pin 70. Coupling portion 36' is identically configured to that of coupling portion 36 of FIGS. 2A-2G except that the extension portion 48' differs from extension portion 48 in its length and end surface 50', which is pointed. It will be understood that the drive pin 70 is located within a hand piece (e.g., hand piece 24 of FIG. 1) and that only the portions of the drive pin 70 that relate to the engagement of the coupling portion 36' are shown. In an initial stage FIG. 6A, the coupling portion 36' inserted within the lumen 74 of the drive pin 70 and the tang 38c has not yet contacted any components (i.e. surfaces 78a-b, 80a-b, 90a-b, 92a-b, 94a-b) of the drive pin 70. In FIG. 6B, the tang 38c is further inserted proximally within the lumen 74 of the drive pin 70. It can be seen that the tang 38c is not properly aligned for operable engagement with the drive pin 70 as the interface walls 56a, 56b are not aligned with the guide surfaces 78a, 78b as would indicate alignment of the interface surfaces 74a, 74b with respective drive surfaces 90a, 90b. In FIGS. 6C and 7), one ramp 54a of the misaligned tang 38c is seen to contact the guide surface 78a (only one ramp 54a and guide surface 78a is visible, however, it will be understood that the other ramp 54b and guide surface 78b would appear as a mirror image on the opposite side of the drive pin 70). Upon contact with the guide surface 78a and with continued insertion forces applied by a user, the tang 38c is urged via each ramp 54a, 54b and/or interface wall 56a, 56b into proper alignment, along the guide surface 78a into the fully coupled or seated position, which is best illustrated in FIG. 6D. Once in the fully seated and operable position of FIG. 6D, the coupled surgical cutting tool (e.g., 22) and hand piece (e.g., 24) are assembled and the drive pin 70 can transfer rotational movement to the coupling portion 36' for correspondingly rotating the cutting head (e.g., 32). With reference to FIG. 7, rotational movement in a clockwise or counterclockwise direction fully seats the interface surfaces 46a, 46b of the tang 38c with the drive surfaces 90a, 90b of the drive pin 70 to rotate the coupling portion 36', and correspondingly rotate, a cutting head interconnected thereto. As will be understood by one of ordinary skill in the art, hand pieces of the present disclosure can be of a variety of configurations and can include additional components for rotatably supporting and operating the drive pin and/or facilitating manual release of the surgical cutting tool.

Although only the engagement of the coupling portion 36' is illustrated with respect to the drive pin 70, it will be understood in view of the present disclosure that engagement of the coupling portions and tangs illustrated in FIGS. 2A-4G is conducted in an identical manner and will the relationship between the drive pin 70 and the respective coupling portion 36, 136, 236 will interface and operate in an identical or substantially identical manner. In sum, all explanations associated with the surfaces and edges of the coupling portion 36' with respect to the drive pin 70 are equally applicable to all embodiments of the disclosure and their respective corresponding features.

Although the present disclosure has been described with reference to preferred embodiments, workers skilled in the art will recognize that changes can be made in form and detail without departing from the spirit and scope of the present disclosure.

What is claimed is:

1. A connecting portion including:
   a tang and a distal portion interconnected by an intermediate stem portion; wherein the intermediate stem portion defines a central axis; further wherein the tang includes:
   an extension portion coaxially aligned with the central axis;
   a first interface surface defining a first plane that is parallel with the central axis; the first interface surface terminating at a first end surface oriented perpendicular to the first plane;
   a first ramp portion extending distally from the first end surface adjacent the extension portion at a first angle of 5 to 85 degrees with respect to the first interface surface;
   a second interface surface defining a second plane that is parallel with the central axis; the second interface surface terminating at a second end surface oriented perpendicular to the second plane; and
   a second ramp portion extending distally from the second end surface adjacent the extension portion at a second angle of 5 to 85 degrees.

2. The connecting portion of claim 1, wherein the second end surface is approximately 180 degrees from the first end surface.

3. The connecting portion of claim 1, wherein an arcuate, first interface wall extends radially away from the first interface surface.

4. The connecting portion of claim 3, wherein the first interface wall extends between the second ramp portion and a convergence point, which is a most proximal point at which the first interface wall contacts the first interface surface.

5. The connecting portion of claim 1, wherein the extension portion terminates at a tip.

6. The connecting portion of claim 5, wherein the tip is domed.

7. The connecting portion of claim 5, wherein the tip defines a planar surface that is perpendicular to the central axis.

8. The connecting portion of claim 1, wherein the extension portion terminates adjacent the first end surface.

9. The connecting portion of claim 1, wherein the first and second interface surfaces are planar.

10. The connecting portion of claim 1, wherein the first and second ramp portions are helical with respect to the extension portion.

11. The connecting portion of claim 1, wherein the extension portion is cylindrical.

12. The connecting portion of claim 1, wherein the first interface surface is identically configured with respect to the second interface surface.

13. The connecting portion of claim 1, wherein the connecting portion has first and second sides, each side including one of the first or second interface surfaces; wherein the first side is a mirror image of the second side.

14. The connecting portion of claim 1, wherein the first ramp defines a straight outer edge.

15. The connecting portion of claim 1, wherein the first interface surface has a maximum width in the range of 0.25 mm to 2.0 mm.

16. A surgical cutting system for use in dissection of bone, biomaterials and/or other tissue, the surgical cutting system comprising:
   a hand piece including a drive pin;
   a cutting tool including a cutting head and a coupling portion coupled to the cutting head such that rotation of the coupling portion correspondingly rotates the cutting head; wherein the coupling portion can releasably connect the cutting tool to the hand piece; wherein the coupling portion includes:
      a tang and a distal portion interconnected by an intermediate stem portion; wherein the intermediate stem portion defines a central axis; further wherein the tang includes:
         an extension portion coaxially aligned with the central axis;
         a first interface surface defining a first plane that is parallel with the central axis; the first interface surface terminating at a first end surface oriented perpendicular to the first plane;
         a first ramp portion extending distally from the first end surface adjacent the extension portion at a first angle of 5 to 85 degrees with respect to the first interface surface;
         a second interface surface defining a second plane that is parallel with the central axis; the second interface surface terminating at a second end surface oriented perpendicular to the second plane; and
         a second ramp portion extending distally from the second end surface adjacent the extension portion at a second angle of 5 to 85 degrees.

17. The surgical cutting system of claim 16, wherein an arcuate, first interface wall extends radially away from a first drive surface.

18. The surgical cutting system of claim 16, wherein the coupling portion has first and second sides; wherein the first side is a mirror image of the second side.

19. The surgical cutting system of claim 16, wherein the first ramp portion defines a straight outer edge.

20. The surgical cutting system of claim 16, wherein the first ramp portion is helical.

* * * * *